United States Patent
Friedman et al.

(10) Patent No.: US 10,646,372 B2
(45) Date of Patent: May 12, 2020

(54) SYSTEMS AND METHODS FOR TREATING AN EYE WITH A MASK DEVICE

(71) Applicant: Avedro, Inc., Waltham, MA (US)

(72) Inventors: Marc D. Friedman, Needham, MA (US); Desmond Adler, Bedford, MA (US)

(73) Assignee: Avedro, Inc., Waltham, MA (US)

( * ) Notice: Subject to any disclaimer, the term of this patent is extended or adjusted under 35 U.S.C. 154(b) by 256 days.

(21) Appl. No.: 15/369,647

(22) Filed: Dec. 5, 2016

(65) Prior Publication Data

US 2017/0156926 A1   Jun. 8, 2017

Related U.S. Application Data

(60) Provisional application No. 62/262,900, filed on Dec. 3, 2015.

(51) Int. Cl.
*A61M 37/00* (2006.01)
*A61F 9/00* (2006.01)
(Continued)

(52) U.S. Cl.
CPC ............ *A61F 9/0026* (2013.01); *A61F 9/008* (2013.01); *A61F 9/04* (2013.01); *A61M 13/00* (2013.01);
(Continued)

(58) Field of Classification Search
CPC . A61F 9/0026; A61F 9/04; A61M 2202/0208; A61M 35/00;
(Continued)

(56) References Cited

U.S. PATENT DOCUMENTS 6,155,995 A    12/2000  Lin
6,946,440 B1   9/2005   DeWoolfson et al.
(Continued)

FOREIGN PATENT DOCUMENTS

CN    202526539 U    11/2012

OTHER PUBLICATIONS

International Search Report and Written Opinion issued in co-pending International Patent Application No. PCT/US2016065010, Federal Institute of Industrial Property of Russia (ISA/RU), dated Apr. 6, 2017, 7 pages.

*Primary Examiner* — Rebecca E Eisenberg
(74) *Attorney, Agent, or Firm* — McDonnell Boehnen Hulbert & Berghoff LLP

(57) ABSTRACT

An eye treatment positions a mask device over first and second eyes. A posterior side of the mask device is proximate to the face and the anterior side is distal from the face. The mask device includes an outer wall extending between the anterior and posterior sides and defining a chamber extending across the first and second eyes. The anterior side includes a first transmission region that allows a photoactivating light for the first eye to be delivered into a first section of the chamber positioned over the first eye. The anterior side includes a second transmission region that allows a photoactivating light for the second eye to be delivered into the second section positioned over the second eye. The system includes at least one gas source storing a gas that is different than ambient air. The system includes a gas delivery system that delivers the gas into the chamber.

27 Claims, 15 Drawing Sheets

(51) Int. Cl.
*A61F 9/04* (2006.01)
*A61F 9/008* (2006.01)
*A61M 13/00* (2006.01)
*A61N 5/06* (2006.01)
*A61N 5/067* (2006.01)

(52) U.S. Cl.
CPC .... *A61N 5/062* (2013.01); *A61F 2009/00872* (2013.01); *A61M 2202/0208* (2013.01); *A61N 2005/067* (2013.01); *A61N 2005/0648* (2013.01); *A61N 2005/0661* (2013.01)

(58) Field of Classification Search
CPC ...... A61N 2005/0648; A61N 2005/067; A61N 5/062; A61N 2005/0661; A61K 41/0042
See application file for complete search history.

(56) References Cited

U.S. PATENT DOCUMENTS

| | | | |
|---|---|---|---|
| 7,073,510 B2 | 7/2006 | Redmond et al. | |
| 7,727,544 B2 | 6/2010 | Schwartz et al. | |
| 8,414,911 B2 | 4/2013 | Mattson et al. | |
| 8,574,277 B2 | 11/2013 | Muller et al. | |
| 8,758,309 B2 | 6/2014 | Nakamura | |
| 2002/0124843 A1 | 9/2002 | Skiba et al. | |
| 2007/0049913 A1 | 3/2007 | Grenon et al. | |
| 2007/0203478 A1 | 8/2007 | Herekar | |
| 2008/0015660 A1 | 1/2008 | Herekar | |
| 2009/0149923 A1 | 6/2009 | Herekar | |
| 2010/0057060 A1* | 3/2010 | Herekar | A61F 9/008 606/4 |
| 2010/0069894 A1 | 3/2010 | Mrochen et al. | |
| 2011/0060267 A1 | 3/2011 | DeWoolfson et al. | |
| 2011/0118654 A1 | 5/2011 | Muller et al. | |
| 2011/0237999 A1 | 9/2011 | Muller et al. | |
| 2011/0264082 A1 | 10/2011 | Mrochen et al. | |
| 2011/0301524 A1 | 12/2011 | Bueler et al. | |
| 2013/0245536 A1* | 9/2013 | Friedman | A61K 41/00 604/20 |
| 2014/0194957 A1 | 7/2014 | Rubinfeld et al. | |
| 2014/0249509 A1 | 9/2014 | Rubinfeld et al. | |
| 2014/0275935 A1 | 9/2014 | Walsh et al. | |
| 2015/0088231 A1 | 3/2015 | Rubinfeld et al. | |
| 2015/0126921 A1 | 5/2015 | Rubinfeld et al. | |
| 2015/0174161 A1 | 6/2015 | Rubinfeld et al. | |
| 2016/0310319 A1 | 10/2016 | Friedman et al. | |
| 2016/0310758 A1 | 10/2016 | Friedman et al. | |

\* cited by examiner

SYSTEMS AND METHODS FOR TREATING AN EYE WITH A MASK DEVICE

CROSS REFERENCE TO RELATED APPLICATIONS

This application claims priority to, and the benefit of, U.S. Provisional Patent Application No. 62/262,900, filed Dec. 3, 2015, the contents of which are incorporated entirely herein by reference.

BACKGROUND

Field

The present disclosure pertains to systems and methods for treating disorders of the eye, and more particularly, to systems and methods that employ a mask device to treat an eye with a photosensitizer, e.g., cross-linking treatment.

Description of Related Art

Cross-linking treatments may be employed to treat eyes suffering from disorders, such as keratoconus. In particular, keratoconus is a degenerative disorder of the eye in which structural changes within the cornea cause it to weaken and change to an abnormal conical shape. Cross-linking treatments can strengthen and stabilize areas weakened by keratoconus and prevent undesired shape changes.

Cross-linking treatments may also be employed after surgical procedures, such as Laser-Assisted in situ Keratomileusis (LASIK) surgery. For instance, a complication known as post-LASIK ectasia may occur due to the thinning and weakening of the cornea caused by LASIK surgery. In post-LASIK ectasia, the cornea experiences progressive steepening (bulging). Accordingly, cross-linking treatments can strengthen and stabilize the structure of the cornea after LASIK surgery and prevent post-LASIK ectasia.

SUMMARY

According to aspects of the present disclosure, systems and methods employ a mask device to treat an eye with a photosensitizer, e.g., cross-linking treatment. For instance, according to one embodiment, a system for treating eyes includes a mask device configured to be positioned over first and second eyes of a face. The mask device includes an anterior side and a posterior side. The posterior side is configured to be positioned proximate to the face and the anterior side configured to be positioned distally from the face. The mask device includes an outer wall extending at least between the anterior side and the posterior side. The outer wall defines a chamber extending across the first and second eyes. The chamber includes a first section and a second section. The first section is configured to be positioned over the first eye. The second section is configured to be positioned over the second eye. The anterior side includes a first transmission region disposed over the first section and a second transmission region disposed over the second section. The first transmission region allows a first photoactivating light for the first eye to be delivered into the first section. The second transmission region allows a second photoactivating light for the second eye to be delivered into the second section. The system includes at least one gas source storing a gas that is different than ambient air. The system includes a gas delivery system coupling the at least one gas source to the mask device. The gas delivery system is configured to deliver the stored gas into the chamber of the mask device.

According to another embodiment, a method for treating eyes includes positioning a mask device over first and second eyes of a face. The mask device includes an anterior side and a posterior side. The posterior side is configured to be positioned proximate to the face and the anterior side is configured to be positioned distally from the face. The mask device includes an outer wall extending at least between the anterior side and the posterior side. The outer wall defining a chamber extending across the first and second eyes. The chamber includes a first section and a second section. The first section is configured to be positioned over the first eye. The second section is configured to be positioned over the second eye. The anterior side includes a first transmission region disposed over the first section and a second transmission region disposed over the second section. The method includes at least one of delivering a first photoactivating light to the first eye via the first transmission region, or delivering a second photoactivating light to the second eye via the second transmission region. The method includes delivering a gas different than ambient air from at least one gas source into the chamber of the mask device. The at least one gas source is coupled to the mask device via a gas delivery system.

Figure 1:
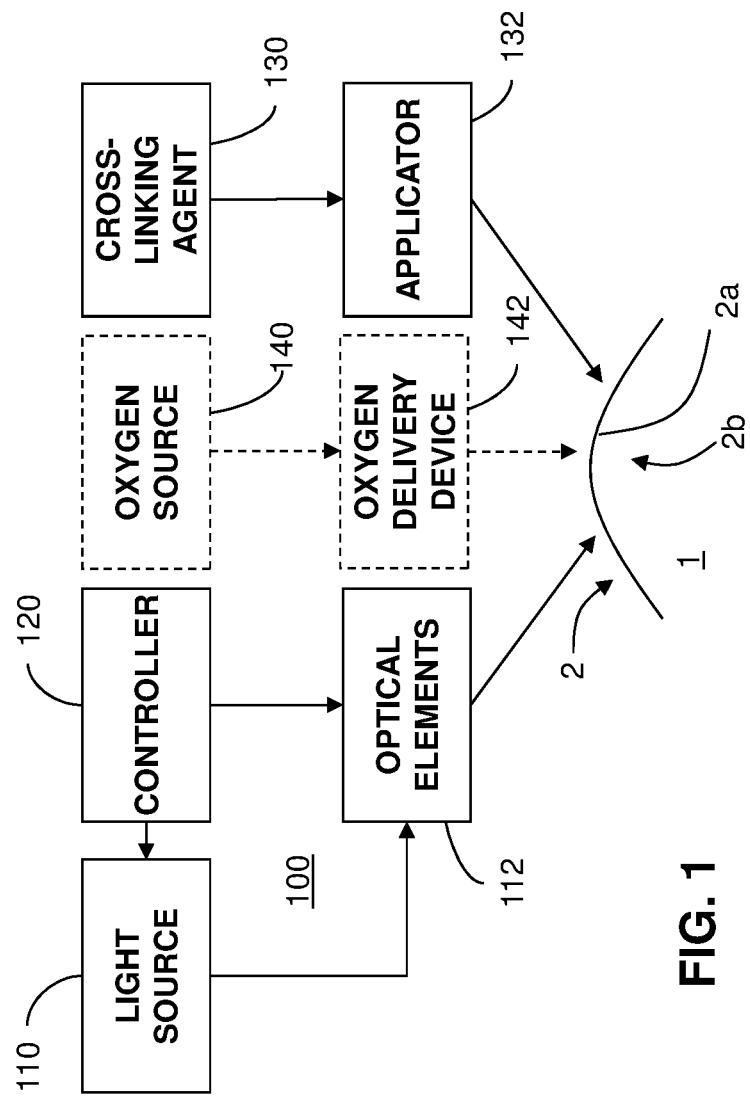
FIG. 1 illustrates an example system that delivers a cross-linking agent and photoactivating light to a cornea of an eye in order to generate cross-linking of corneal collagen, according to aspects of the present disclosure.

While the present disclosure is susceptible to various modifications and alternative forms, a specific embodiment thereof has been shown by way of example in the drawings and will herein be described in detail. It should be understood, however, that it is not intended to limit the present disclosure to the particular forms disclosed, but on the contrary, the intention is to cover all modifications, equivalents, and alternatives falling within the spirit of the present disclosure.

DESCRIPTION

FIG. 1 illustrates an example treatment system 100 for generating cross-linking of collagen in a cornea 2 of an eye 1. The treatment system 100 includes an applicator 132 for applying a cross-linking agent 130 to the cornea 2. In example embodiments, the applicator 132 may be an eye dropper, syringe, or the like that applies the photosensitizer 130 as drops to the cornea 2. The cross-linking agent 130 may be provided in a formulation that allows the cross-linking agent 130 to pass through the corneal epithelium 2a and to underlying regions in the corneal stroma 2b. Alternatively, the corneal epithelium 2a may be removed or otherwise incised to allow the cross-linking agent 130 to be applied more directly to the underlying tissue.

The treatment system 100 includes an illumination device with a light source 110 and optical elements 112 for directing light to the cornea 2. The light causes photoactivation of the cross-linking agent 130 to generate cross-linking activity in the cornea 2. For example, the cross-linking agent may include riboflavin and the photoactivating light may include ultraviolet A (UVA) (e.g., approximately 365 nm) light. Alternatively, the photoactivating light may include another wavelength, such as a visible wavelength (e.g., approximately 452 nm). As described further below, corneal cross-linking improves corneal strength by creating chemical bonds within the corneal tissue according to a system of photochemical kinetic reactions. For instance, riboflavin and the photoactivating light may be applied to stabilize and/or strengthen corneal tissue to address diseases such as keratoconus or post-LASIK ectasia.

The treatment system 100 includes one or more controllers 120 that control aspects of the system 100, including the light source 110 and/or the optical elements 112. In an implementation, the cornea 2 can be more broadly treated with the cross-linking agent 130 (e.g., with an eye dropper, syringe, etc.), and the photoactivating light from the light source 110 can be selectively directed to regions of the treated cornea 2 according to a particular pattern.

The optical elements 112 may include one or more mirrors or lenses for directing and focusing the photoactivating light emitted by the light source 110 to a particular pattern on the cornea 2. The optical elements 112 may further include filters for partially blocking wavelengths of light emitted by the light source 110 and for selecting particular wavelengths of light to be directed to the cornea 2 for photoactivating the cross-linking agent 130. In addition, the optical elements 112 may include one or more beam splitters for dividing a beam of light emitted by the light source 110, and may include one or more heat sinks for absorbing light emitted by the light source 110. The optical elements 112 may also accurately and precisely focus the photoactivating light to particular focal planes within the cornea 2, e.g., at a particular depths in the underlying region 2b where cross-linking activity is desired.

Moreover, specific regimes of the photoactivating light can be modulated to achieve a desired degree of cross-linking in the selected regions of the cornea 2. The one or more controllers 120 may be used to control the operation of the light source 110 and/or the optical elements 112 to precisely deliver the photoactivating light according to any combination of: wavelength, bandwidth, intensity, power, location, depth of penetration, and/or duration of treatment (the duration of the exposure cycle, the dark cycle, and the ratio of the exposure cycle to the dark cycle duration).

The parameters for photoactivation of the cross-linking agent 130 can be adjusted, for example, to reduce the amount of time required to achieve the desired cross-linking. In an example implementation, the time can be reduced from minutes to seconds. While some configurations may apply the photoactivating light at an irradiance of 5 mW/cm$^2$, larger irradiance of the photoactivating light, e.g., multiples of 5 mW/cm$^2$, can be applied to reduce the time required to achieve the desired cross-linking. The total dose of energy absorbed in the cornea 2 can be described as an effective dose, which is an amount of energy absorbed through an area of the corneal epithelium 2a. For example the effective dose for a region of the corneal surface 2A can be, for example, 5 J/cm$^2$, or as high as 20 J/cm$^2$ or 30 J/cm$^2$. The effective dose described can be delivered from a single application of energy, or from repeated applications of energy.

The optical elements 112 of the treatment system 100 may include a digital micro-mirror device (DMD) to modulate the application of photoactivating light spatially and temporally. Using DMD technology, the photoactivating light from the light source 110 is projected in a precise spatial pattern that is created by microscopically small mirrors laid out in a matrix on a semiconductor chip. Each mirror represents one or more pixels in the pattern of projected light. With the DMD one can perform topography guided cross-linking. The control of the DMD according to topography may employ several different spatial and temporal irradiance and dose profiles. These spatial and temporal dose profiles may be created using continuous wave illumination but may also be modulated via pulsed illumination by pulsing the illumination source under varying frequency and duty cycle regimes as described above. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined. This allows for specific amounts of spatially determined corneal cross-linking. This spatially determined cross-linking may be combined with dosimetry, interferometry, optical coherence tomography (OCT), corneal topography, etc., for pre-treatment planning and/or real-time monitoring and modulation of corneal cross-linking during treatment. Aspects of a dosimetry system are described in further detail below. Additionally, pre-clinical patient information may be combined with finite element biomechanical computer modeling to create patient specific pre-treatment plans.

To control aspects of the delivery of the photoactivating light, embodiments may also employ aspects of multiphoton excitation microscopy. In particular, rather than delivering a single photon of a particular wavelength to the cornea 2, the treatment system 100 may deliver multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than light of shorter wavelengths. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules in the cross-linking agent 130 to generate the photochemical kinetic reactions described further below. When a cross-linking agent molecule simultaneously absorbs both photons, it absorbs enough energy to release reactive radicals in the corneal tissue. Embodiments may also utilize lower energy photons such that a cross-linking agent molecule must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

A large number of conditions and parameters affect the cross-linking of corneal collagen with the cross-linking agent 130. For example, the irradiance and the dose of photoactivating light affect the amount and the rate of cross-linking.

When the cross-linking agent 130 is riboflavin in particular, the UVA light may be applied continuously (continuous wave (CW)) or as pulsed light, and this selection has an effect on the amount, the rate, and the extent of cross-linking. If the UVA light is applied as pulsed light, the duration of the exposure cycle, the dark cycle, and the ratio of the exposure cycle to the dark cycle duration have an effect on the resulting corneal stiffening. Pulsed light illumination can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately 1000/1 to approximately 1/1000; the irradiance may be between approximately 1 mW/cm$^2$ to approximately 1000 mW/cm$^2$ average irradiance, and the pulse rate may be between approximately 0.01 HZ to approximately 1000 Hz or between approximately 1000 Hz to approximately 100,000 Hz.

The treatment system 100 may generate pulsed light by employing a DMD, electronically turning the light source 110 on and off, and/or using a mechanical or opto-electronic (e.g., Pockels cells) shutter or mechanical chopper or rotating aperture. Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea to allow for various amounts of refractive correction. These refractive corrections, for instance, may involve combinations of myopia, hyperopia, astigmatism, irregular astigmatism, presbyopia and complex corneal refractive surface corrections because of ophthalmic conditions such as keratoconus, pellucid marginal disease, post-LASIK ectasia, and other conditions of corneal biomechanical alteration/degeneration, etc. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Although example embodiments may employ stepwise on/off pulsed light functions, it is understood that other functions for applying light to the cornea may be employed to achieve similar effects. For example, light may be applied to the cornea according to a sinusoidal function, sawtooth function, or other complex functions or curves, or any combination of functions or curves. Indeed, it is understood that the function may be substantially stepwise where there may be more gradual transitions between on/off values. In addition, it is understood that irradiance does not have to decrease down to a value of zero during the off cycle, and may be above zero during the off cycle. Desired effects may be achieved by applying light to the cornea according to a curve varying irradiance between two or more values.

Examples of systems and methods for delivering photoactivating light are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No. 2013/0245536, filed Mar. 15, 2013 and titled "Systems and Methods for Corneal Cross-Linking with Pulsed Light," the contents of these applications being incorporated entirely herein by reference.

The addition of oxygen also affects the amount of corneal stiffening. In human tissue, $O_2$ content is very low compared to the atmosphere. The rate of cross-linking in the cornea, however, is related to the concentration of $O_2$ when it is irradiated with photoactivating light. Therefore, it may be advantageous to increase or decrease the concentration of $O_2$ actively during irradiation to control the rate of cross-linking until a desired amount of cross-linking is achieved. Oxygen may be applied during the cross-linking treatments in a number of different ways. One approach involves supersaturating the riboflavin with $O_2$. Thus, when the riboflavin is applied to the eye, a higher concentration of $O_2$ is delivered directly into the cornea with the riboflavin and affects the reactions involving $O_2$ when the riboflavin is exposed to the photoactivating light. According to another approach, a steady state of $O_2$ (at a selected concentration) may be maintained at the surface of the cornea to expose the cornea to a selected amount of $O_2$ and cause $O_2$ to enter the cornea. As shown in FIG. 1, for instance, the treatment system 100 also includes an oxygen source 140 and an oxygen delivery device 142 that optionally delivers oxygen at a selected concentration to the cornea 2. Example systems and methods for applying oxygen during cross-linking treatments are described, for example, in U.S. Pat. No. 8,574,277, filed Oct. 21, 2010 and titled "Eye Therapy," U.S. Patent Application Publication No. 2013/0060187, filed Oct. 31, 2012 and titled "Systems and Methods for Corneal Cross-Linking with Pulsed Light," the contents of these applications being incorporated entirely herein by reference.

When riboflavin absorbs radiant energy, especially light, it undergoes photoactivation. There are two photochemical kinetic pathways for riboflavin photoactivation, Type I and Type II. Some of the reactions involved in both the Type I and Type II mechanisms are as follows:

Common Reactions:

$$Rf \to Rf_1^*, l; \quad (r1)$$

$$Rf_1^* \to Rf, \kappa 1; \quad (r2)$$

$$Rf_1^* \to Rf_3^*, \kappa 2; \quad (r3)$$

Type I Reactions:

$$Rf_3^* + DH \to RfH^\bullet + D^\bullet, \kappa 3; \quad (r4)$$

$$2RfH^\bullet \to Rf + RfH_2, \kappa 4; \quad (r5)$$

Type II Reactions:

$$Rf_3^* + O_2 \to Rf + O_2^1, \kappa 5; \quad (r6)$$

$$DH + D_2^1 \to D_{ox}, \kappa 6; \quad (r7)$$

$$D_{ox} + DH \to D-D, \kappa 7; \quad CXL \quad (r8)$$

In the reactions described herein, Rf represents riboflavin in the ground state. $Rf^*_1$ represents riboflavin in the excited singlet state. $Rf^*_3$ represents riboflavin in a triplet excited state. $Rf^{\bullet-}$ is the reduced radical anion form of riboflavin. $RfH^\bullet$ is the radical form of riboflavin. $RfH_2$ is the reduced form of riboflavin. DH is the substrate. $DH^{\bullet+}$ is the intermediate radical cation. $D^\bullet$ is the radical. $D_{ox}$ is the oxidized form of the substrate.

Riboflavin is excited into its triplet excited state $Rf^*_3$ as shown in reactions (r1) to (r3). From the triplet excited state $Rf^*_3$, the riboflavin reacts further, generally according to Type I or Type II mechanisms. In the Type I mechanism, the substrate reacts with the excited state riboflavin to generate radicals or radical ions, respectively, by hydrogen atoms or electron transfer. In Type II mechanism, the excited state riboflavin reacts with oxygen to form singlet molecular oxygen. The singlet molecular oxygen then acts on tissue to produce additional cross-linked bonds.

Oxygen concentration in the cornea is modulated by UVA irradiance and temperature and quickly decreases at the beginning of UVA exposure. Utilizing pulsed light of a specific duty cycle, frequency, and irradiance, input from both Type I and Type II photochemical kinetic mechanisms can be employed to achieve a greater amount of photochemical efficiency. Moreover, utilizing pulsed light allows regulating the rate of reactions involving riboflavin. The rate of reactions may either be increased or decreased, as needed, by regulating, one of the parameters such as the irradiance, the dose, the on/off duty cycle, riboflavin concentration, soak time, and others. Moreover, additional ingredients that affect the reaction and cross-linking rates may be added to the cornea.

If UVA radiation is stopped shortly after oxygen depletion, oxygen concentrations start to increase (replenish). Excess oxygen may be detrimental in the corneal cross-linking process because oxygen is able to inhibit free radical photopolymerization reactions by interacting with radical species to form chain-terminating peroxide molecules. The pulse rate, irradiance, dose, and other parameters can be adjusted to achieve a more optimal oxygen regeneration rate. Calculating and adjusting the oxygen regeneration rate is another example of adjusting the reaction parameters to achieve a desired amount of corneal stiffening.

Oxygen content may be depleted throughout the cornea, by various chemical reactions, except for the very thin corneal layer where oxygen diffusion is able to keep up with the kinetics of the reactions. This diffusion-controlled zone will gradually move deeper into the cornea as the reaction ability of the substrate to uptake oxygen decreases.

Riboflavin is reduced (deactivated) reversibly or irreversibly and/or photo-degraded to a greater extent as irradiance increases. Photon optimization can be achieved by allowing reduced riboflavin to return to ground state riboflavin in Type I reactions. The rate of return of reduced riboflavin to ground state in Type I reactions is determined by a number of factors. These factors include, but are not limited to, on/off duty cycle of pulsed light treatment, pulse rate frequency, irradiance, and dose. Moreover, the riboflavin concentration, soak time, and addition of other agents, including oxidizers, affect the rate of oxygen uptake. These and other parameters, including duty cycle, pulse rate frequency, irradiance, and dose can be selected to achieve more optimal photon efficiency and make efficient use of both Type I as well as Type II photochemical kinetic mechanisms for riboflavin photosensitization. Moreover, these parameters can be selected in such a way as to achieve a more optimal chemical amplification effect.

In addition to the photochemical kinetic reactions (r1)-(r8) above, however, the present inventors have identified the following photochemical kinetic reactions (r9)-(r26) that also occur during riboflavin photoactivation:

$$Rf_3^* \to Rf, \kappa 8; \quad (r9)$$

$$Rf_3^* + Rf \to 2RfH^\bullet, \kappa 9; \quad (r10)$$

$$RfH_2 + O_2 \to RfH^\bullet + H^+ + O_2^-, \kappa 10; \quad (r11)$$

$$RfH^\bullet + O_2 \to Rf + H^+ + O_2^-, \kappa 11; \quad (r12)$$

$$2RfH_2 + O_2^- \to 2RfH^\bullet + H_2O_2, \kappa 12; \quad (r13)$$

$$2RfH^\bullet + O_2^- \to 2Rf + H_2O_2, \kappa 13; \quad (r14)$$

$$RfH^\bullet + H_2O_2 \to OH^\bullet + Rf + H_2O, \kappa 14; \quad (r15)$$

$$OH^\bullet + DH \to D^\bullet + H_2O, \kappa 15; \quad (r16)$$

$$D^\bullet + D^\bullet \to D-D, \kappa 16; \quad CXL \quad (r17)$$

$$O_2^1 \to O_2, \kappa 18; \quad (r18)$$

$$D^\bullet + RfH_2 \to RfH^\bullet + DH, \kappa 19; \quad (r19)$$

$$Rf + Rf \underset{\kappa_a^-}{\overset{\kappa_a^+}{\rightleftharpoons}} A_1, \kappa_a = \kappa_a^+/\kappa_a^- \quad (r20)$$

$$RfH_2 + RfH_2 \underset{\kappa_a^-}{\overset{\kappa_a^+}{\rightleftharpoons}} A_2, \kappa_a = \kappa_a^+/\kappa_a^- \quad (r21)$$

$$Rf + RfH_2 \underset{\kappa_b^-}{\overset{\kappa_b^+}{\rightleftharpoons}} A_3, \kappa_b = \kappa_b^+/\kappa_b^- \quad (r22)$$

$$Rf_1^* + A \to Rf + A, \kappa_{1a} \quad (r23)$$

$$Rf_3^* + A \to Rf + A, \kappa_{3a} \quad (r24)$$

$$2O_2^- \to O_2 + H_2O_2, \kappa_{12} \quad (r25)$$

$$OH^\circ + CXL \to \text{inert products}, \kappa_{OH} \quad (r26)$$

Figure 2A:
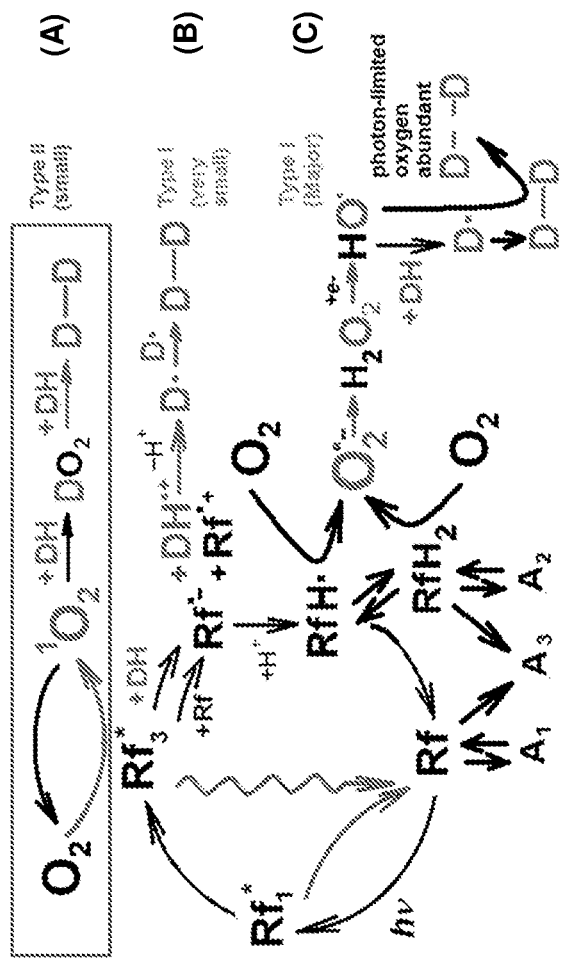
FIG. 2A illustrates a diagram for photochemical kinetic reactions involving riboflavin and photoactivating light (e.g., ultraviolet A (UVA) light) applied during a corneal cross-linking treatment, according to aspects of the present disclosure.

FIG. 2A illustrates a diagram for the photochemical kinetic reactions provided in reactions (r1) through (r26) above. The diagram summarizes photochemical transformations of riboflavin (Rf) under UVA photoactivating light and its interactions with various donors (DH) via electron transfer. As shown, cross-linking activity occurs: (A) through the presence of singlet oxygen in reactions (r6) through (r8) (Type II mechanism); (B) without using oxygen in reactions (r4) and (r17) (Type I mechanism); and (C) through the presence of peroxide ($H_2O_2$), superoxide ($O_2^-$), and hydroxyl radicals (.OH) in reactions (r13) through (r17).

As shown in FIG. 2A, the present inventors have also determined that the cross-linking activity is generated to a greater degree from reactions involving peroxide, superoxide, and hydroxyl radicals. Cross-linking activity is generated to a lesser degree from reactions involving singlet oxygen and from non-oxygen reactions. Some models based on the reactions (r1)-(r26) can account for the level of cross-linking activity generated by the respective reactions. For instance, where singlet oxygen plays a smaller role in generating cross-linking activity, models may be simplified by treating the cross-linking activity resulting from singlet oxygen as a constant.

All the reactions start from $Rf_3^*$ as provided in reactions (r1)-(r3). The quenching of $Rf_3^*$ occurs through chemical reaction with ground state Rf in reaction (r10), and through deactivation by the interaction with water in reaction (r9).

As described above, excess oxygen may be detrimental in corneal cross-linking process. As shown in FIG. 2A, when the system becomes photon-limited and oxygen-abundant, cross-links can be broken from further reactions involving superoxide, peroxide, and hydroxyl radicals. Indeed, in some cases, excess oxygen may result in net destruction of cross-links versus generation of cross-links.

As described above, a large variety of factors affect the rate of the cross-linking reaction and the amount of biomechanical stiffness achieved due to cross-linking. A number of these factors are interrelated, such that changing one factor may have an unexpected effect on another factor. However, a more comprehensive model for understanding the relationship between different factors for cross-linking treatment is provided by the photochemical kinetic reactions (r1)-(r26) identified above. Accordingly, systems and methods can adjust various parameters for cross-linking treatment according to this photochemical kinetic cross-linking model, which provides a unified description of oxygen dynamics and cross-linking activity. The model can be employed to evaluate expected outcomes based on different combinations of treatment parameters and to identify the combination of treatment parameters that provides the desired result. The parameters, for example, may include, but are not limited to: the concentration(s) and/or soak times of the applied cross-linking agent; the dose(s), wavelength(s), irradiance(s), duration(s), and/or on/off duty cycle(s) of the photoactivating light; the oxygenation conditions in the tissue; and/or presence of additional agents and solutions.

Figure 2B:
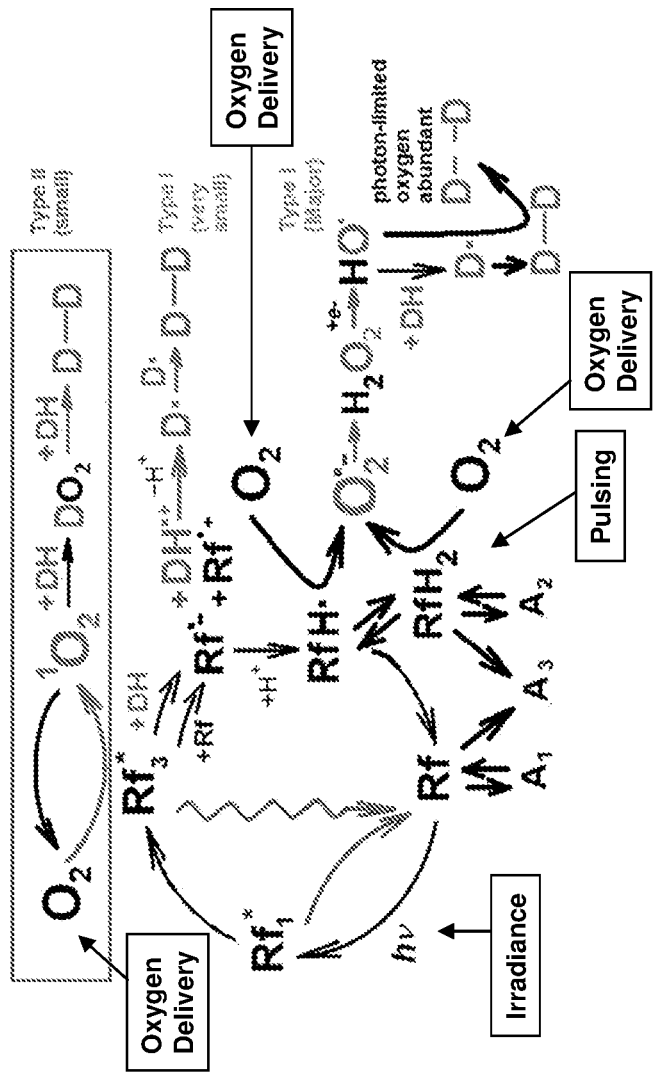
FIG. 2B illustrates a diagram for parameters that can affect the photochemical kinetic reactions shown in FIG. 2A.

As shown in FIG. 2B, aspects of the system of reactions can be affected by different parameters. For instance, the irradiance at which photoactivating light is delivered to the system affects the photons available in the system to generate $Rf_3^*$ for subsequent reactions. Additionally, delivering greater oxygen into the system drives the oxygen-based reactions. Meanwhile, pulsing the photoactivating light affects the ability of the reduced riboflavin to return to ground state riboflavin by allowing additional time for oxygen diffusion. Of course, other parameters can be varied to control the system of reactions.

Figure 3:
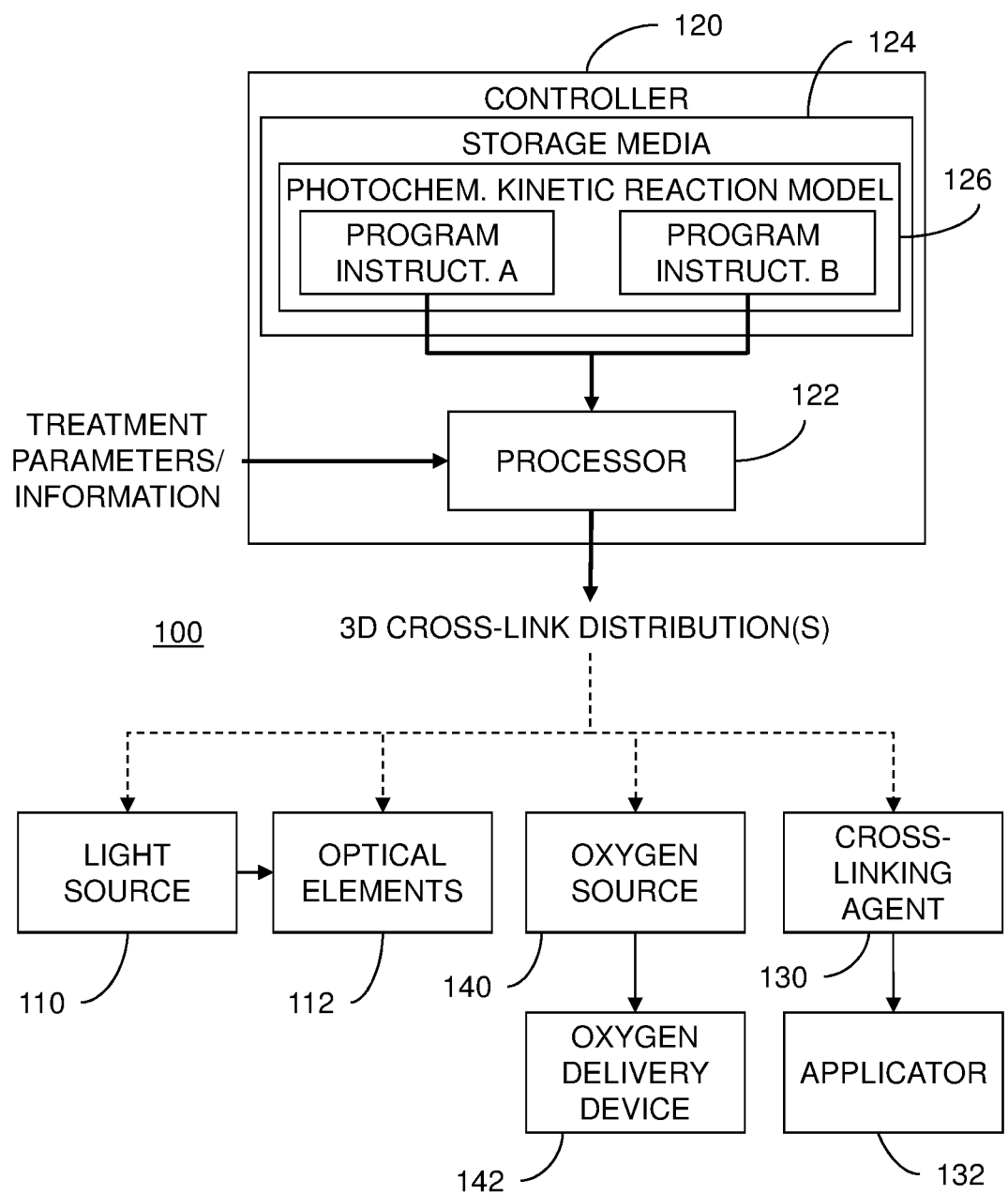
FIG. 3 illustrates an example system employing a model of photochemical kinetic reactions according to aspects of the present disclosure.

According to an embodiment, FIG. 3 illustrates the example system 100 employing a model based on the photochemical kinetic reactions (r1)-(r26) identified above to determine an amount of cross-linking that results from treatment parameters and/or other related information. The controller 120 includes a processor 122 and computer-readable storage media 124. The storage media 124 stores program instructions for determining an amount of cross-linking when the photoactivating light from the light source 110 is delivered to a selected region of a cornea treated with a cross-linking agent. In particular, a photochemical kinetic model 126 based on the reactions (r1)-(r26) may include a first set of program instructions A for determining cross-linking resulting from reactions involving reactive oxygen species (ROS) including combinations of peroxides, superoxides, hydroxyl radicals, and/or singlet oxygen and a second set of program instructions B for determining cross-linking from reactions not involving oxygen. The controller 120 receives input relating to treatment parameters and/or other related information. The controller 120 can then execute the program instructions A and B to output information relating to three-dimensional cross-link distribution(s) for the selected region of the cornea based on the input. The three-dimensional cross-link distribution(s) may then be employed to determine how to control aspects of the light source 110, the optical elements 112, the cross-linking agent 130, the applicator 132, the oxygen source 140, and/or oxygen delivery device 142 in order to achieve a desired treatment in selected region of the cornea. (Of course, the system 100 shown in FIG. 3 and this process can be used for treatment of more than one selected region of the same cornea.)

According to one implementation, the three-dimensional cross-link distribution(s) may be evaluated to calculate a threshold depth corresponding to a healing response due to the cross-links and an effect of the reactive-oxygen species in the selected region of the cornea. Additionally or alternatively, the three-dimensional cross-link distribution(s) may be evaluated to calculate a biomechanical tissue stiffness threshold depth corresponding to a biomechanical tissue response in the selected region of the cornea. The information on the depth of the healing response and/or the biomechanical tissue stiffness in the cornea can be employed to determine how to control aspects of the light source 110, the optical elements 112, the cross-linking agent 130, the applicator 132, the oxygen source 140, and/or oxygen delivery device 142. Certain healing response and/or biomechanical tissue stiffness may be desired or not desired at certain depths of the cornea.

Figure 4:
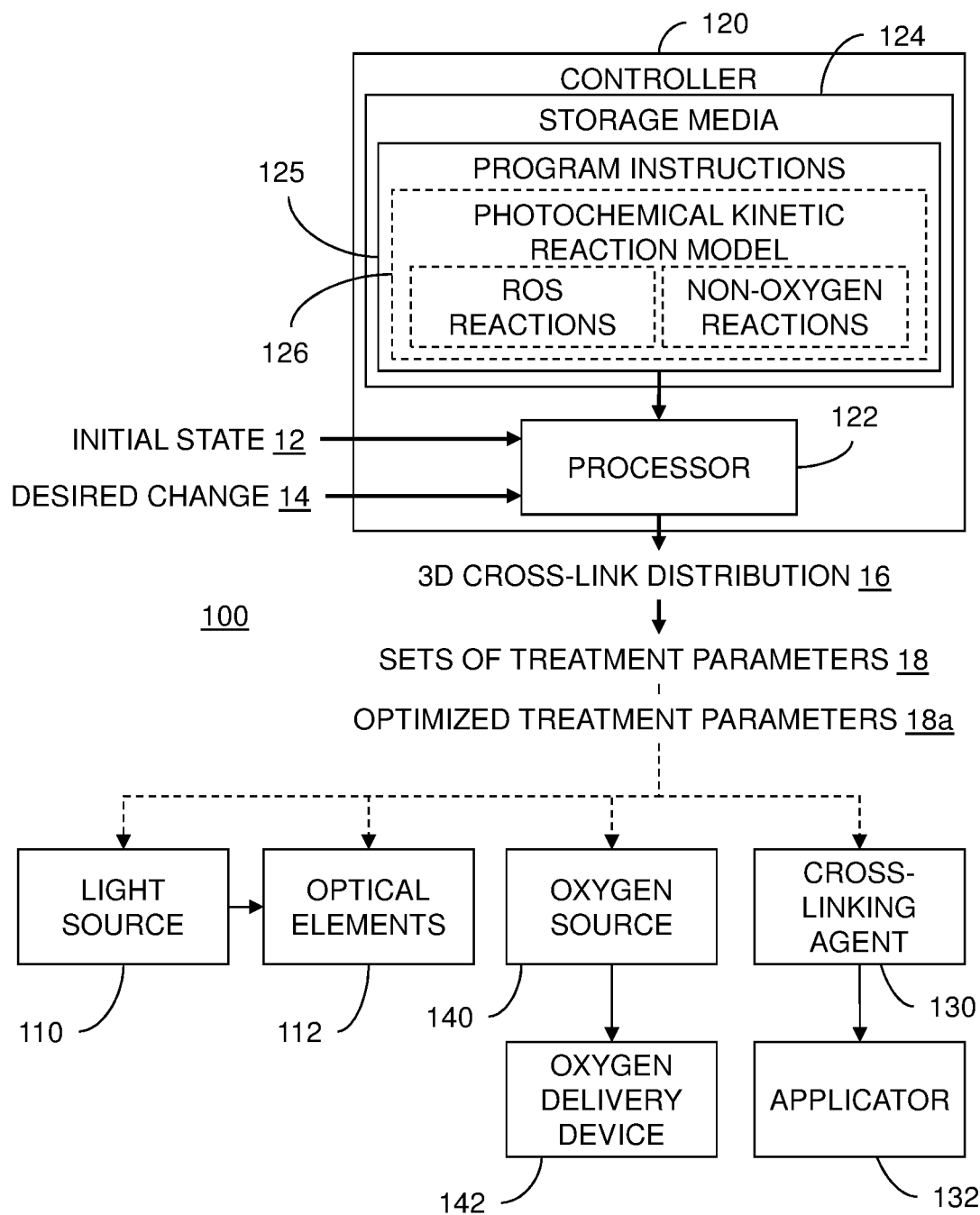
FIG. 4 illustrates an example system employing a model of photochemical kinetic reactions to provide treatment parameters for achieving desired biomechanical changes according to aspects of the present disclosure.

According to another embodiment, FIG. 4 illustrates the example system 100 employing the photochemical kinetic model 126 to determine treatment parameters for achieving desired biomechanical changes in the cornea, e.g., a refractive correction. As in FIG. 3, the controller 120 includes the processor 122 and the computer-readable storage media 124. In the example of FIG. 4, however, the storage media 124 stores program instructions 125 for determining what treatment parameters may be employed to achieve desired biomechanical changes. The program instructions 125 are based on the photochemical kinetic model 126 which employ the reactions (r1)-(r26) to determine cross-linking resulting from (i) reactions involving reactive oxygen species (ROS) including combinations of peroxides, superoxides, hydroxyl radicals, and/or singlet oxygen and (ii) reactions not involving oxygen.

Using the photochemical kinetic model 126, a three-dimensional distribution of resulting cross-links throughout the treated corneal tissue can be determined for a combination of treatment parameters. As described above, parameters for cross-linking treatment may include: the concentration(s) and/or soak times of the applied cross-linking agent; the dose(s), wavelength(s), irradiance(s), duration(s), on/off duty cycle(s), and/or other illumination parameters for the photoactivating light; the oxygenation conditions in the tissue; and/or presence of additional agents and solutions. The resulting distribution of cross-links determined from the photochemical kinetic model 126 can be correlated to a particular biomechanical change in the cornea. For instance, there is a correlation between the distribution of cross-links and refractive change.

As shown in FIG. 4, the controller 120 receives an input 12 relating to the initial biomechanical state of the cornea and an input 14 indicating a desired biomechanical change for the cornea, e.g., for refractive correction. The initial biomechanical state, for instance, can be determined according to approaches described in U.S. Patent Application Publication No. 2012/0215155 referenced above. In some cases, the input 12 may be provided by a measurement system communicatively coupled to the controller 120. It is understood that the initial biomechanical state may reflect the state of the cornea prior to any treatment or during a treatment.

The inputs 12, 14 may be expressed in terms of corneal topography (i.e., shape), corneal strength (i.e., stiffness), and/or corneal thickness. For instance, the desired biomechanical change for refractive correction may be determined from a correction specified (by a practitioner) in diopters, e.g., "a 1.5 diopter correction."

A desired biomechanical change in the cornea can be correlated to a particular distribution of cross-links as determined by the photochemical kinetic model 126. As such, the controller 120 can execute the program instructions 125 to determine the particular distribution of cross-links 16 that can generate the desired biomechanical change specified by the input 14 in a cornea having the initial biomechanical state specified by the input 12. After determining the distribution of cross-links 16 for the desired biomechanical change, the controller 120 can prescribe a set of treatment parameters for achieving the specified distribution of cross-links.

The distribution of cross-links 16 might be achieved in many cases by more than one set of treatment parameters. For instance, depending on the photochemical kinetic reactions, similar distributions of cross-links may be achieved by applying: (i) a lower dose of photoactivating light for a longer amount of time, or (ii) a higher dose of photoactivating light for a shorter amount of time. Therefore, more than one set of treatment parameters 18 for achieving the distribution of cross-links 16 may be identified.

With more than one possible set of treatment parameters 18, a practitioner can optimize the treatment for certain preferred parameters, such as treatment time or dose of photoactivating light. For instance, the practitioner may optimize the treatment parameters to achieve shorter treatment times. For this preference, the controller 120 may prescribe a set of illumination parameters that provide a larger dose of photoactivating light that yields the distribution of cross-links 16 over shorter illumination durations. Conversely, the practitioner may optimize the treatment parameters to employ smaller doses of photoactivating light. For this second preference, the controller 120 may prescribe a set of illumination parameters that provide a smaller dose of photoactivating light that yields the distribution of cross-links 16 over longer illumination durations.

In general, to achieve the distribution of cross-links 16, the controller 120 may identify any of the different combinations 18 of values for a set of treatment parameters A, B, C, D, E, etc., as described above. The practitioner can set preferences for one or more of these treatment parameters. For instance, the practitioner may initially set a preferred value or range of preferred values for parameter A. In response, the controller 120 can specify combinations of values for the remaining parameters B, C, D, E, etc., that meet the preference for parameter A while achieving the distribution of cross-links 16. The practitioner may make selections for the values of the parameters B, C, D, and/or E, etc., based on further preferences to arrive at an optimized set of treatment parameters 18a. The process of optimizing the treatment parameters may be iterative as the values for the treatment parameters are incrementally tuned to meet preferences having varying priorities.

In some embodiments, the practitioner may manage the optimization process through a series of selections and other inputs via a user interface (not shown) coupled to the controller 120. In some cases, the inputs 12, 14 may also be provided through such a user interface.

The final set of treatment parameters 18a can then be employed to determine how to control aspects of the light source 110, the optical elements 112, the cross-linking agent 130, the applicator 132, the oxygen source 140, oxygen delivery device 142, etc., in order to achieve a desired treatment in selected region of the cornea.

Figure 5:
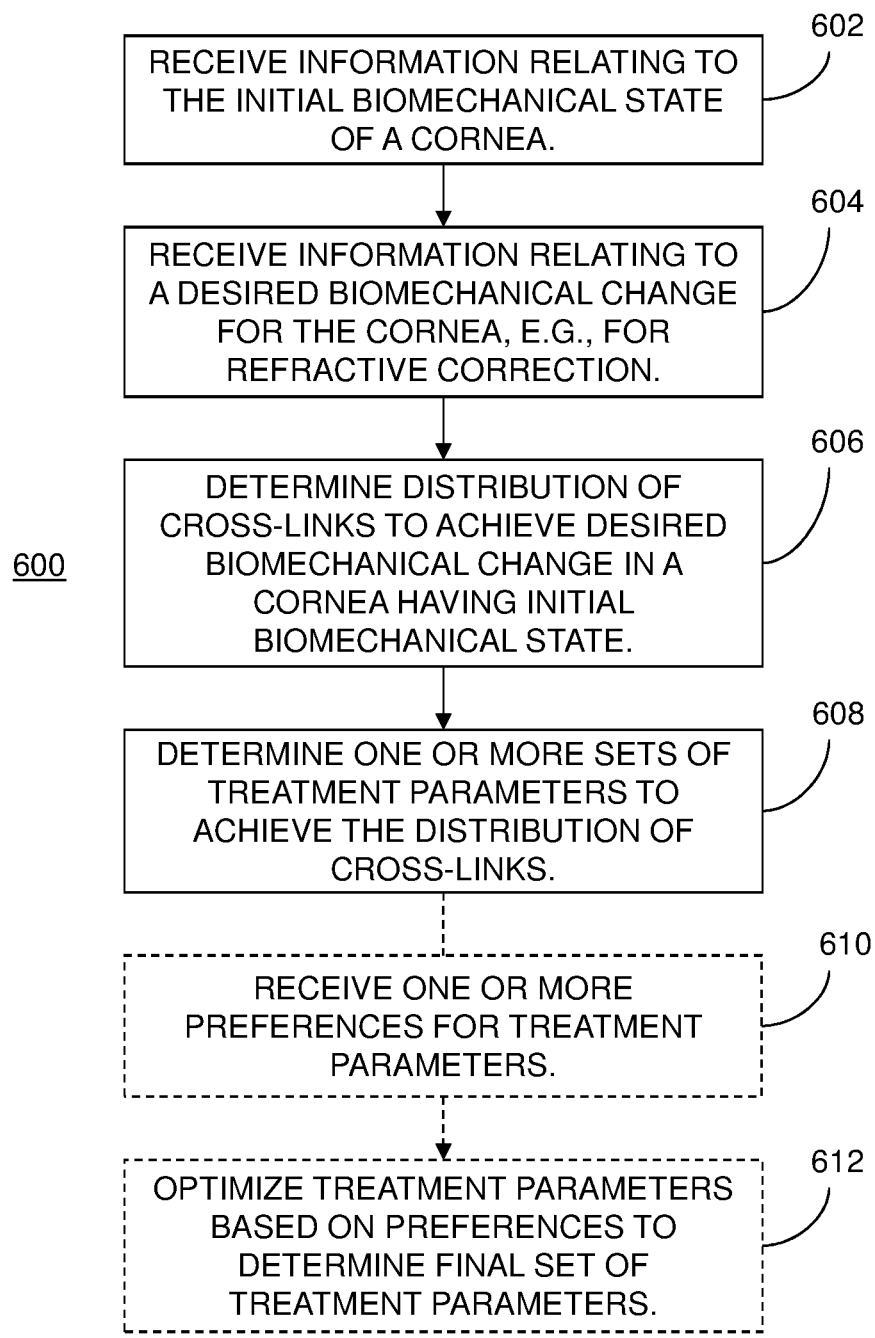
FIG. 5 an example method employing a model of photochemical kinetic reactions to determine treatment parameters for achieving desired biomechanical changes according to aspects of the present disclosure.

Correspondingly, FIG. 5 illustrates an example method 600 for employing a model of photochemical kinetic reactions (r1)-(r26) to determine treatment parameters for achieving desired biomechanical changes. In step 602, information relating to the initial biomechanical state of a cornea is received. In step 604, information relating to a desired biomechanical change for the cornea, e.g., for refractive correction, is received. In step 606, a distribution of cross-links is determined to achieve the desired biomechanical change in a cornea having the initial biomechanical state. In step 608, one or more sets of treatment parameters are determined to achieve the distribution of cross-links. In association with step 608, one or more preferences for treatment parameters may be received in step 610, and the treatment parameters may be optimized in step 612 based on the one or more preferences to determine a final set of treatment parameters that can be implemented in a treatment system (e.g., the example system 100) to achieve the distribution of cross-links.

Further aspects of the photochemical kinetic reactions provided in reactions (r1)-(r26) are described in U.S. patent application Ser. No. 15/140,184, filed Apr. 27, 2016 and titled "Systems and Methods for Cross-Linking Treatments of an Eye," the contents of which are incorporated entirely herein by reference.

Figure 6:
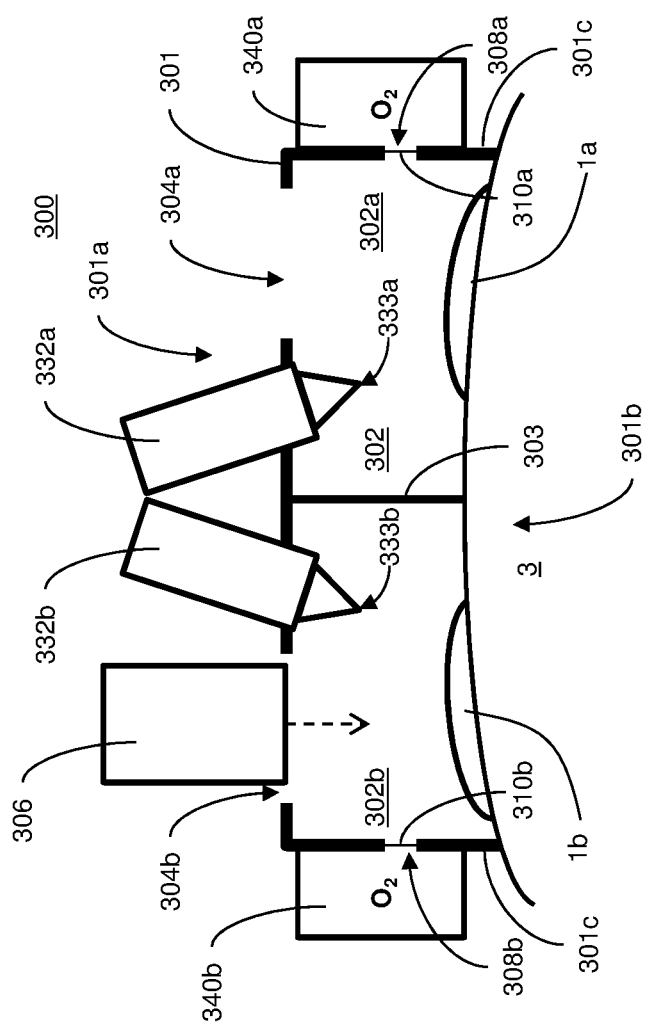
FIG. 6 illustrates an example system for applying eye treatments with a mask device, according to aspects of the present disclosure.

FIG. 6 illustrates an example treatment system 300 for applying cross-linking treatment to both eyes 1a, b of a patient. Aspects of the treatment systems described above may be incorporated into the treatment system 300. As shown in FIG. 6, the treatment system 300 includes a mask device 301 that is configured to be positioned on the patient's face 3 and to fit over both the right eye 1a and the left eye 1b. The mask device 301 may be kept in position on the patient's face 3 by a strap (not shown) that can be worn around the patient's head. As such, in some aspects, the mask device 301 may resemble a pair of goggles or the like. Alternatively, medical tape or the like may be applied to the mask device 301 and the face 3 to keep the mask device 301 in position. Alternatively, the mask device 301 may be shaped to rest stably against the patient's face 3 without additional support while the patient is lying on his/her back. In some cases, a speculum may be applied to each eye 1a, b to keep the eyelids from closing during the treatment. In such cases, the mask device 301 may be dimensioned to fit around or otherwise accommodate the use of the specula. The mask device 301 may be employed for cross-linking treatments with an intact corneal epithelium (also known as "epi-on") or without an intact corneal epithelium (also known as "epi-off").

The mask device 301 is defined by a body having an anterior side 301a and a posterior side 301b, where the anterior side 301a is positioned distally from the face 3 and the posterior side 301b is positioned proximate to (e.g., against) the face 3. The posterior side 301b may define an opening for receiving the face 3. The body includes an outer wall 301c extending at least between the anterior side 301a and the posterior side 301b. The wall 301c defines a chamber 302 that extends across the right and left eyes 1a, b. The chamber 302 includes a right section 302a that is positioned over the right eye 1a and a left section 302b that is positioned over the left eye 1b. Each section 302a, b facilitates the application of a cross-linking treatment to the cornea in the respective eye 1a, b. The sections 302a, b may be physically divided by an internal wall 303 as shown in FIG. 6 to reduce any likelihood that treatment of one eye will affect treatment of the other eye. Aspects of the mask device 301 may be formed from plastic and/or other suitable materials.

A right applicator 332a and a left applicator 332b may be implemented for the right section 302a and the left section 302b, respectively. As shown in FIG. 6, the applicators 332a, b may be coupled to the mask device 301. The right applicator 332a may apply a first photosensitizer solution, such as a first riboflavin formulation, to the cornea of the right eye 1a. The left applicator 332b may apply a second photosensitizer solution, such as a second riboflavin formulation, to the cornea of the left eye 1b. For instance, each applicator 332a, b may include aspects of an eye dropper, syringe, or the like, including a respective opening 333a, b from which the photosensitizer solution can be dripped onto or otherwise delivered to the cornea. The first photosensitizer solution and the second photosensitizer solution may have similar or different formulations depending on the similarities or differences between the treatments for the right and left eyes 1a, b. Furthermore, the first photosensitizer solution and the second photosensitizer solution may be applied to the respective right and left eyes 1a, b with similar or different soak times.

In addition to employing the applicators 332a, b to deliver an initial dose of photosensitizer solution to the eyes 1a, b, the applicators 332a, b (or other similar applicators) may be further employed to irrigate the eyes 1a, b periodically to keep them moist during treatment. For instance, the eyes 1a, b may be irrigated with saline or additional photosensitizer solution. Additionally, the applicators 332a, b or other similar applicators may apply solutions containing other agents. For instance, such agents may enhance the amount of cross-linking activity, particularly with epi-on treatments. Other agents may quench the cross-linking activity generated by the cross-linking agent. Yet other agents may include an antibiotic to provide antimicrobial treatment.

The anterior side 301a includes a right transmission region 304a disposed over the right section 302a and a left transmission region 304b disposed over the left section 302b. The right transmission region 304a allows a first photoactivating light to be delivered into the right section 302a and to the right eye 1a. The left transmission region 304b allows a second photoactivating light to be delivered into the left section 302b and to the left eye 1b. As shown in FIG. 6, the right transmission region 304a and the left transmission region 304b are apertures through which the first photoactivating light and the second photoactivating light can be delivered, respectively. The outer wall 301c may provide structure for the anterior side 301a and may define the apertures for the right transmission region 304a and the left transmission region 304b. If an eye 1a, b has been treated with a photosensitizer solution including riboflavin for instance, the corresponding photoactivating light may be ultraviolet light as described above.

The treatment system 300 may also include an illumination device 306, which may be positioned relative to the mask device 300 to deliver the first photoactivating light to the right eye 1a or the second photoactivating light to the left eye 1b. In some embodiments, the illumination device 306 may be separately supported, e.g., by a stand, over the right transmission region 304a or the left transmission region 304b.

The illumination device 306 may include aspects of the light source 110 and the optical elements 112 as described above. Additionally, the controller 120 may be employed to control the light source 110 and/or the optical elements 112. The first photoactivating light or the second photoactivating light may be delivered according to similar or different parameters depending on the similarities or differences between the treatments for the right and left eyes 1a, b. For instance, the dose, irradiation, pattern, pulsing/continuous wave, and other treatment parameters for the photoactivating light may be controlled as described above.

The mask device 301 also allows a concentration of oxygen gas to be delivered to the eyes 1a, b. As described above, oxygen gas enhances or otherwise affects cross-linking activity during photoactivation. As shown in FIG. 6, each section 302a, b may include respective oxygen sources 340a, b coupled to the mask device 301. The oxygen from the right oxygen source 340a can be selectively released into the right section 302a through a right port 308a in the mask device 301. The oxygen from the left oxygen source 340b can be selectively released into the left section 302b through a left port 308b in the mask device 301. The release can be controlled by removing a seal 310a, b that is placed between the oxygen source 304a, b and the port 308a, b, respectively. For instance, the seal 310a, b may be a pull-off tab that can be manually removed by the practitioner. Although the first transmission region 304a and the second transmission region 304b may be apertures, the chamber 302 is able to hold sufficient oxygen from the oxygen sources 340a, b to control the cross-linking activity as desired. Indeed, oxygen gas is heavier than the ambient air that may fill the chamber 302 prior to delivery of the oxygen gas, so the oxygen gas remains in the chamber 302 while the ambient air may flow from the chamber 302 (e.g., if the patient's face is lying on his/her back). As described above, the posterior side 301b of the mask device 301 may define an opening to receive the face 3. To promote effective delivery of the oxygen gas to the eyes 1a, b, the outer wall 301c along the posterior side 301b is preferably contoured to form a substantially complete seal against the face 3 (e.g., to prevent the escape of the oxygen gas particularly posterior of the corneal surface). In some embodiments, the oxygen gas may be delivered at substantially 2.5 L/min, but may be effectively delivered at rates as low as approximately 1.0 L/min for instance.

If only one illumination device is available, the eyes 1a, b can be alternately treated with the photoactivating light.

For instance, as shown in FIG. 6, the illumination device 306 is positioned over the left transmission region 304b to deliver the second photoactivating light. The same illumination device 306 may be repositioned over the right transmission region 304a to deliver the first photoactivating light to the right eye 1a after the second photoactivating light has been delivered to the left eye 1b.

Advantageously, the mask device 301 allows one eye to be treated with photoactivating light, while allowing the other eye to be treated with the photosensitizer solution. As shown in FIG. 6, the right eye 1a can be soaked with the first photosensitizer solution from the applicator 332a, while the left eye 1b receives photoactivating light after having already been soaked in the second photosensitizer solution from the applicator 332b. After the application of photoactivating light to the left eye 1b is complete, the illumination device 306 may be repositioned over the right transmission region 304a to deliver the first photoactivating light to the right eye 1a. By allowing both eyes 1a, b to receive some treatment step at the same time, the total treatment time can be reduced significantly even when only one illumination device 306 available. For instance, with the mask device, the single illumination device 306 may be used to treat at least four pairs of eyes in one hour depending on treatment parameters.

In general, the example systems described herein may employ the photochemical kinetic model 126 as described above to determine the treatment parameters for achieving desired biomechanical changes in the cornea. As such, the treatment system 300 may be employed to implement parameters for the delivery of oxygen as well as photoactivating light according to steps determined by the kinetic model 126. In an example implementation, the illumination device 306 may be operated to apply UV light to an eye, e.g., at a low irradiance of 1.5 mW/cm$^2$ or 3 mW/cm$^2$, for an initial period of time, e.g., the first five minutes of a thirty minute treatment. The kinetic model 126 may indicate that the cross-linking activity occurs at a desirable (e.g., optimal) rate without the addition of oxygen gas. However, after the initial period of time, the kinetic model 126 may indicate that the cross-linking activity becomes oxygen-limited. Thus, the treatment provided by the treatment system 300 may introduce oxygen gas from an oxygen source into the chamber 302 after the initial period of time.

Figure 7:
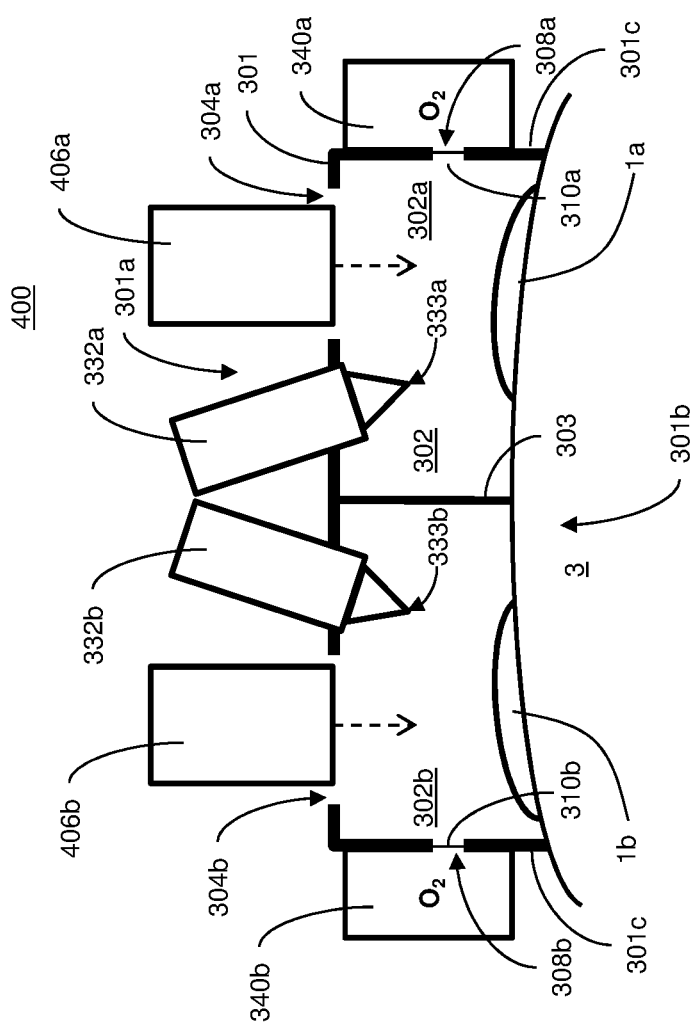
FIG. 7 illustrates another example system for applying eye treatments with a mask device, according to aspects of the present disclosure.

Although the example embodiment in FIG. 6 may employ only one illumination device 306, other embodiments may include more than one illumination device 306. As shown in FIG. 7, an example treatment system 400 may include a right illumination device 406a positioned over the right transmission region 304a and a left illumination device 406b over the left transmission region 304b. As such, the treatment system 400 allows both eyes 1a, b to be treated simultaneously.

Furthermore, although the illumination device 306 in FIG. 6 may be decoupled from the mask device 301, the illumination devices 406a, b or aspects thereof may in some cases be fixedly coupled to the mask device 301.

Figure 8:
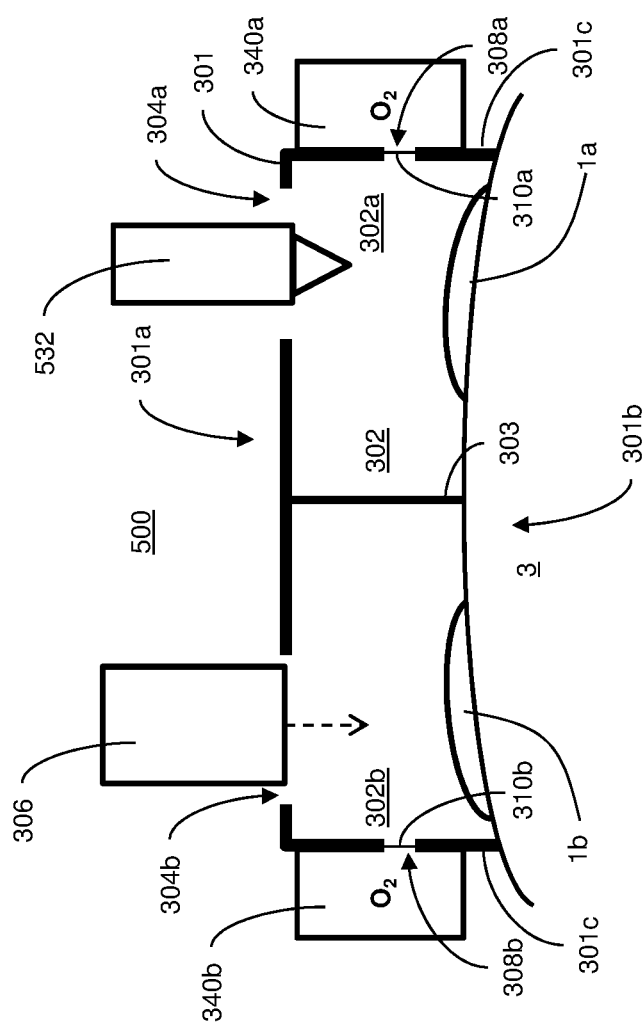
FIG. 8 illustrates yet another example system for applying eye treatments with a mask device, according to aspects of the present disclosure.

Although the applicators 332a, b in the example embodiment of FIG. 6 are coupled to the mask device 301, other embodiments may alternatively decouple such applicators from the mask device 301. As shown in FIG. 8, an example treatment system 500 may include a separate cross-linking applicator 532 that may be selectively repositioned and introduced through the right transmission aperture 304a to apply the first photosensitizer solution to the right eye 1a or the left transmission aperture 304b to apply the second photosensitizer solution to the left eye 1b.

Figure 9:
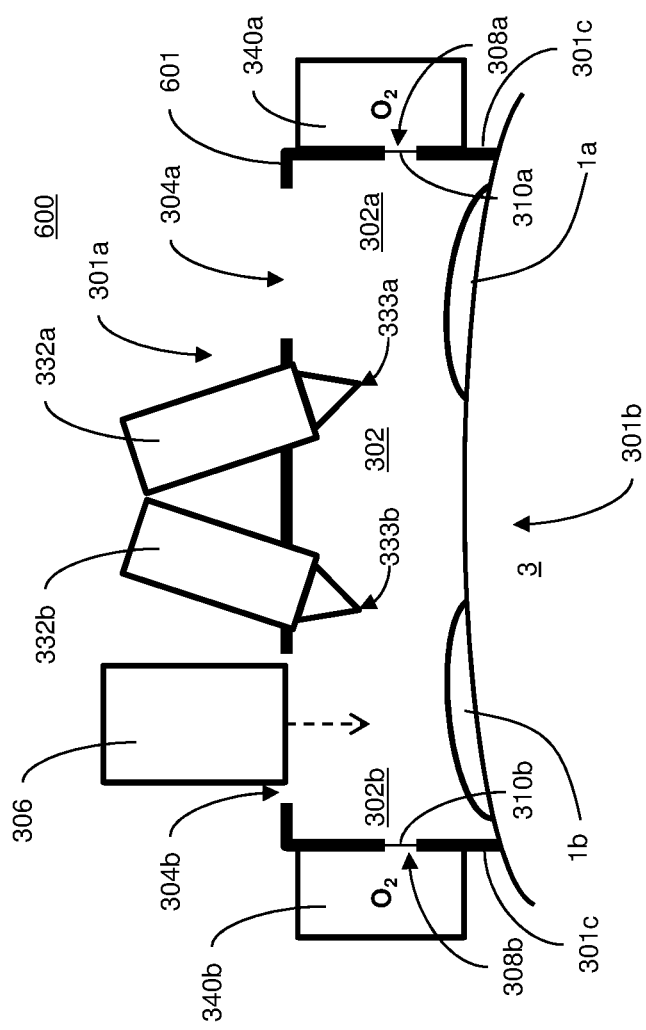
FIG. 9 illustrates a further example system for applying eye treatments with a mask device, according to aspects of the present disclosure.

Although the internal wall 303 may be employed in the example embodiment of FIG. 6 to separate the right section 302a from the left section 302b in the chamber 302, FIG. 9 illustrates an example system 600 with a mask device 601 that omits the use of such a wall in the chamber 302. In this embodiment, the right section 302a and the left section 302b are not (completely) separated by structure(s), so that oxygen gas that enters the right section 302a can flow to the left section 302b, and vice versa. Thus, both ports 308a, b can be used to fill the entire chamber 302 with oxygen gas.

Figure 10:
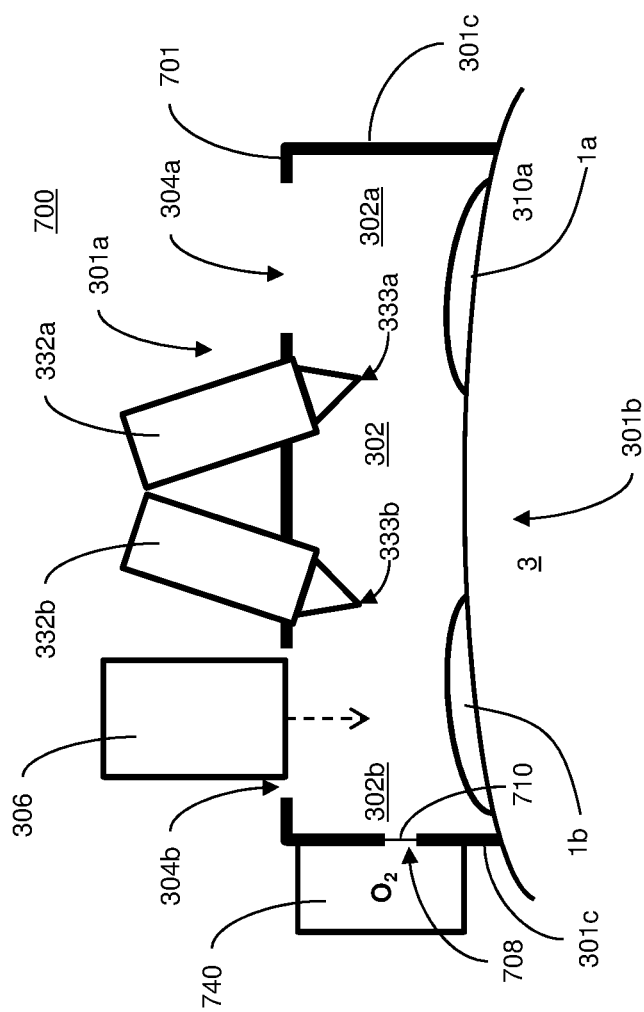
FIG. 10 illustrates yet a further example system for applying eye treatments with a mask device, according to aspects of the present disclosure.

FIG. 10 illustrates an example system 700 that includes a mask device 701 with a single port 708 coupled to an oxygen source 740. The oxygen delivered from the oxygen source 740 via the port 708 fills both the right section 302a and the left section 302b of the chamber 302.

Figure 11:
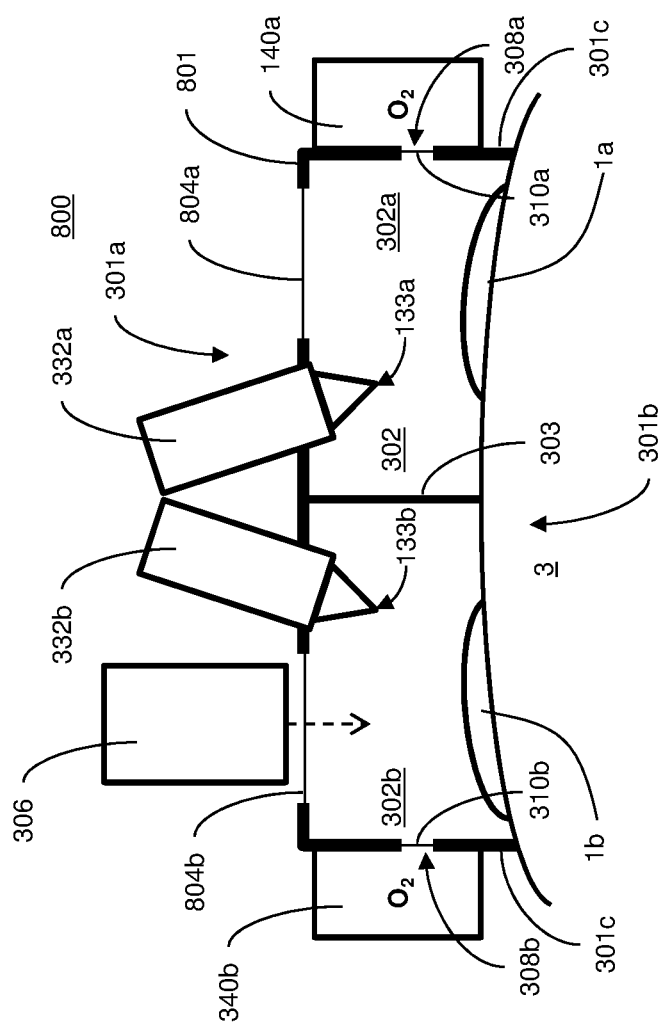
FIG. 11 illustrates an additional example system for applying eye treatments with a mask device, according to aspects of the present disclosure.

Although the right transmission region 304a and the left transmission region 304b in the example embodiment of FIG. 6 may be apertures, FIG. 11 illustrates an example system 800 with a mask device 801 where a right transmission region 804a and a left transmission region 804b are windows formed from translucent material(s) that allow photoactivating light to pass into the chamber 302 and to be applied to the eyes 1a, b according to the desired treatment parameters. Advantageously, the mask device 801 provides an effective enclosure that can retain the oxygen gas delivered into the chamber 302 from the oxygen sources 340a, b. In some cases, such an enclosure allows the oxygen gas to be retained under a desired pressure. In further cases, the mask device 801 may include vents that ensure that oxygen gas does generate undesired pressure in the chamber 302.

Figure 12A:
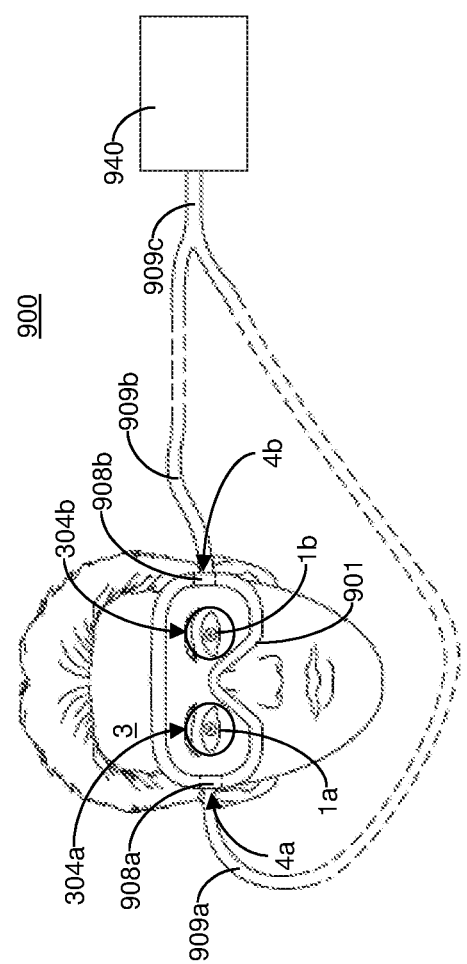
FIG. 12A illustrates an example system for applying eye treatments with a mask, where the treatment system employs an external oxygen gas source according to aspects of the present disclosure.
Figure 12B:
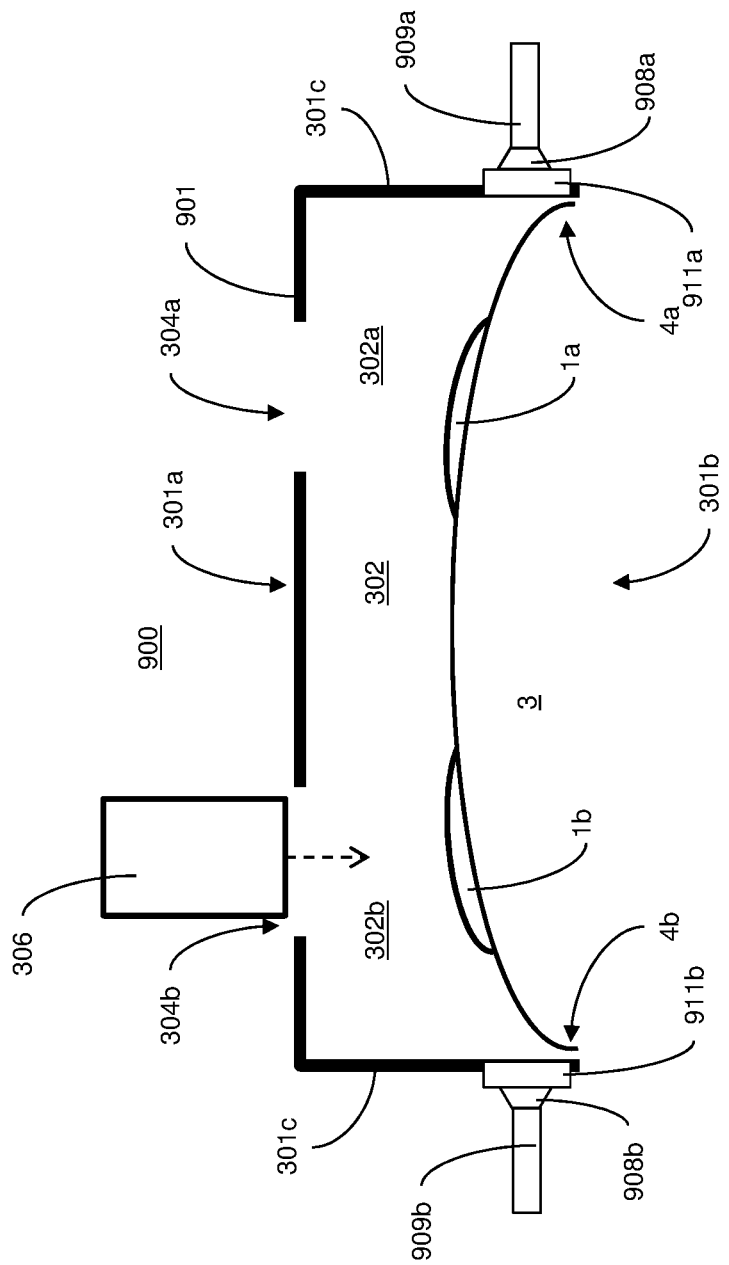
FIG. 12B further illustrates the example system of FIG. 12A, where oxygen gas is delivered from the external oxygen gas source with minimal turbulence/backpressure according to aspects of the present disclosure.

Although the oxygen sources 340a, b in the example embodiment of FIG. 6 are coupled to the mask device 301, other embodiments may employ oxygen source(s) that are spaced away from the mask device. As shown in FIGS. 12A-D, an example treatment system 900 includes a mask device 901 with a right port 908a leading to the right section 302a and a left port 908b leading to the left section 302b. The right port 908a and the left port 908b may be coupled to the same external oxygen source 940 via right and left tubes 909a, b, respectively. The right and left tubes 909a, b may extend to a y-splitter 909c that is coupled to the external oxygen source. For instance, the external oxygen source 940 may be controlled by a valve to deliver the oxygen gas to the chamber 302. If the right section 302a and the left section 302b are not separated by an interior wall as shown in FIG. 12B, the oxygen gas delivered from the oxygen source 940 via both ports 908a, b fills the entire chamber 302. Alternatively, if the right section 302a and the left section 302b are separated by an interior wall, the oxygen gas delivered from the oxygen source 940 via the port 908a, b fills the respective section 302a, b. Alternatively, the right port 908a and the left port 908b may be coupled to separate external oxygen sources via the right and left tubes 909a, b, respectively.

In general, the treatment systems described herein are configured so that the oxygen gas is introduced into the chambers with minimal turbulence and backpressure so that the desired amount of oxygen is predictably delivered to the eyes 1a, b. As also shown in FIG. 12B, such turbulence/backpressure can be minimized by directing the oxygen gas toward the temples 4a, b of the face 3. In particular, the right port 908a leads to a right diffuser 911a that directs the oxygen gas toward the right temple 4a and the left port 908b leads to a left diffuser 911b to direct the oxygen gas toward the left temple 4b. The diffusers 911a, b may be configured to angle the oxygen gas from the respective tubes 909a, b through the opening of the posterior side 301b towards the respective temples 4a, b. In addition to minimizing turbulence and backpressure, the oxygen gas is directed so that it does not flow directly over the eyes 1a, b which minimizes undesired drying of the eyes 1a, b. Once the oxygen gas reaches the temples 4a, b, the oxygen gas flows over the eyes 1a, b. As described above, the oxygen gas is heavier than the ambient air that may fill the chamber 302 prior to delivery of the oxygen gas, so the oxygen gas can remain in the chamber 302 over the eyes 1a, b.

Figure 12C:
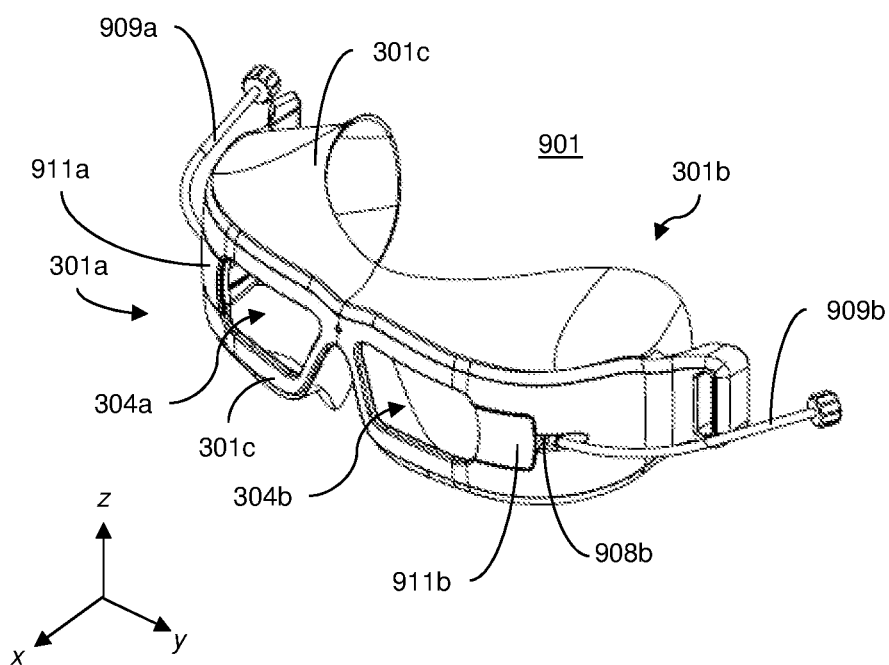
FIG. 12C illustrates a detailed view of the mask device of the example system of FIGS. 12A-B.
Figure 12D:
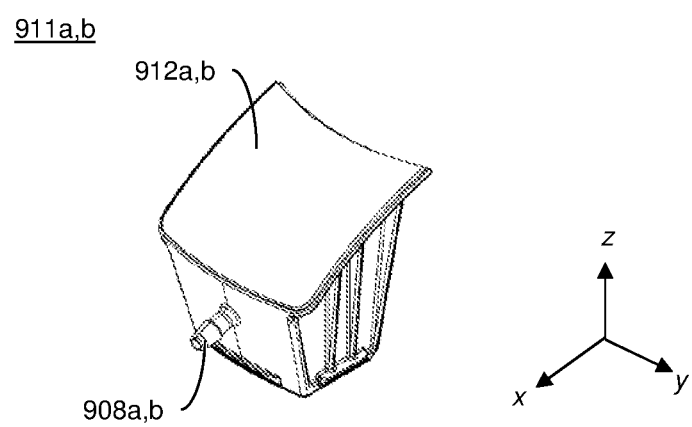
FIG. 12D illustrates an example diffuser for the mask device of FIG. 12C, where the diffuser delivers oxygen gas with minimal turbulence/backpressure according to aspects of the present disclosure.

FIG. 12C further illustrates aspects of the mask device 901. By way of example, the mask device 901 may be approximately 21.5 cm from the right side to the left side along the y-axis as shown, approximately 8.5 cm from top to bottom along the z-axis as shown, and approximately 9.5 cm from anterior side to posterior side along the x-axis as shown. FIG. 12D further illustrates, by way of example, one of the diffusers 911a, b, where a respective angled surface 912a, b and other structures direct the oxygen air to a respective temple 4a, b. As shown, the respective port 908a, b may also be angled (in combination with the angled surface 912a, b) to direct the oxygen air more effectively. By way of example, the diffuser 911a, b may be approximately 2.2 cm along the y-axis as shown, approximately 2.2 cm along the z-axis as shown, and approximately 1.9 cm from along the x-axis as shown.

In general, embodiments can employ at least one gas source storing a gas that is different than ambient air and a gas delivery system coupling the at least one gas source to the mask device, where the gas delivery system delivers the stored gas into the chamber of the body. In the particular embodiments above, the gas provided by the oxygen sources includes an increased concentration of oxygen greater than an ambient concentration of oxygen in the ambient air.

Although the mask device 301 is described above in the context of cross-linking treatments, the mask device 301 may be additionally or alternatively used to provide other treatments for the eyes 1a, b. For instance, the mask device 301 may be employed for antimicrobial treatment. Indeed, the mask device 301 may also apply and photoactivate a photosensitizer, such as riboflavin, for antimicrobial effect. In other antimicrobial treatments, an antibiotic agent may be applied with the applicators 332a, b in combination with oxygen from the oxygen sources 340a, b. Such applications of the antibiotic agent may be more effective than merely applying the antibiotic agent in air. Indeed, lower doses of the antibiotic agent may be employed when a higher concentration of oxygen is provided.

As described above, according to some aspects of the present disclosure, some or all of the steps of the above-described and illustrated procedures can be automated or guided under the control of a controller (e.g., the controller 120). Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the example embodiments of the present disclosure, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the example embodiments, as is appreciated by those skilled in the software art. In addition, the devices and subsystems of the example embodiments can be implemented by the preparation of application-specific integrated circuits or by interconnecting an appropriate network of conventional component circuits, as is appreciated by those skilled in the electrical art(s). Thus, the example embodiments are not limited to any specific combination of hardware circuitry and/or software.

Stored on any one or on a combination of computer readable media, the example embodiments of the present disclosure may include software for controlling the devices and subsystems of the example embodiments, for driving the devices and subsystems of the example embodiments, for enabling the devices and subsystems of the example embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the example embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the present disclosure. It is also contemplated that additional embodiments according to aspects of the present disclosure may combine any number of features from any of the embodiments described herein.

What is claimed is:

1. A system for treating eyes, comprising:
   a mask device configured to be positioned over first and second eyes of a face, the mask device including an anterior side and a posterior side, the posterior side configured to be positioned proximate to the face and the anterior side configured to be positioned distally from the face, the mask device including an outer wall extending at least between the anterior side and the posterior side, the outer wall defining a chamber extending across the first and second eyes, the chamber including a first section and a second section, the first section configured to be positioned over the first eye, the second section configured to be positioned over the second eye, the anterior side including a first transmission region disposed over the first section and a second transmission region disposed over the second section, the first transmission region allowing a first photoactivating light for the first eye to be delivered into the first section, the second transmission region allowing a second photoactivating light for the second eye to be delivered into the second section;

at least one gas source storing a gas that is different than ambient air; and a gas delivery system coupling the at least one gas source to the mask device, the gas delivery system including a first port leading into the first section of the chamber and a second port leading into the second section of the chamber, the gas delivery system configured to deliver the gas into the chamber of the mask device via the first port and the second port, wherein the mask device includes a first diffuser and a second diffuser, the first port leading into the first diffuser and the second port leading into the second diffuser, the first diffuser configured to deliver the gas toward a first temple of the face, and the second diffuser configured to deliver the gas toward a second temple of the face.

2. The system of claim 1, wherein the gas includes an increased concentration of oxygen greater than an ambient concentration of oxygen in the ambient air.

3. The system of claim 1, wherein the at least one gas source includes a first gas source coupled to the mask device and including a first opening allowing a first gas to flow into the first section via the first port, and a second gas source coupled to the mask device and including a second opening allowing a second gas to flow into the second section via the second port.

4. The system of claim 3, wherein the gas delivery system includes a first seal closing the first opening of the first gas source and a second seal closing the second opening of the second gas source, the first seal configured to be removed to selectively allow the first gas to flow into the first section, the second seal configured to be removed to selectively allow the second gas to flow into the second section.

5. The system of claim 1, wherein the at least one gas source includes a gas source spaced away from the mask device, and the gas delivery system includes a first tube extending from the first port to the gas source and a second tube extending from the second port to the gas source.

6. The system of claim 1, further comprising at least one illumination device configured to deliver at least one of the first photoactivating light or the second photoactivating light.

7. The system of claim 1, wherein the first photoactivating light and the second photoactivating light are delivered according to different treatment parameters.

8. The system of claim 1, wherein the first transmission region is a first aperture formed in the anterior side and the second transmission region is a second aperture formed in the anterior side.

9. The system of claim 1, wherein the first transmission region includes a first window formed in the anterior side and the second transmission region is a second window formed in the anterior side.

10. The system of claim 9, wherein the mask device is configured to keep the gas from the at least one gas source at a predetermined pressure.

11. The system of claim 1, further comprising a first solution applicator coupled to the mask device and configured to deliver a first solution to the first eye, and a second solution applicator coupled to the mask device and configured to deliver a second solution to the second eye.

12. The system of claim 11, wherein the first solution and the second solution include different photo sensitizer formulations.

13. The system of claim 1, wherein the gas can flow across the chamber, from the first section to the second section and vice versa.

14. The system of claim 1, wherein the mask device includes an inner wall separating the first section and the second section in the chamber of the mask device.

15. A method for treating eyes, comprising:

positioning a mask device over first and second eyes of a face, the mask device including an anterior side and a posterior side, the posterior side configured to be positioned proximate to the face and the anterior side configured to be positioned distally from the face, the mask device including an outer wall extending at least between the anterior side and the posterior side, the outer wall defining a chamber extending across the first and second eyes, the chamber including a first section and a second section, the first section configured to be positioned over the first eye, the second section configured to be positioned over the second eye, the anterior side including a first transmission region disposed over the first section and a second transmission region disposed over the second section;

at least one of delivering a first photoactivating light to the first eye via the first transmission region, or delivering a second photoactivating light to the second eye via the second transmission region; and delivering a gas different than ambient air from at least one gas source into the chamber of the mask device, the at least one gas source being coupled to the mask device via a gas delivery system, the gas delivery system including a first port leading into the first section of the chamber and a second port leading into the second section of the chamber, the gas delivery system configured to deliver the gas into the chamber of the mask device via the first port and the second port, wherein the mask device includes a first diffuser and a second diffuser, the first port leading into the first diffuser and the second port leading into the second diffuser, the first diffuser configured to deliver the gas toward a first temple of the face, and the second diffuser configured to deliver the gas toward a second temple of the face.

16. The method of claim 15, further comprising at least one of delivering a first photosensitizer solution to the first eye according to a first soak time, or delivering a second photosensitizer solution to the second eye according to a second soak time.

17. The method of claim 16, wherein the first photosensitizer solution and the second photosensitizer solution have different photosensitizer formulations.

18. The method of claim 16, wherein:
the first photosensitizer solution is initially delivered to the first eye;
after the first photosensitizer solution is delivered according to the first soak time, the first photoactivating light is delivered with an illumination device to the first eye;
during delivery of the first photoactivating light to the first eye, the second photosensitizer solution is delivered to the second eye; and
after the first photoactivating light is delivered to the first eye and the second photosensitizer solution is delivered according to the second soak time, the second photoactivating light is delivered with the same illumination device to the second eye.

19. The method of claim 15, wherein the gas includes an increased concentration of oxygen greater than an ambient concentration of oxygen in the ambient air.

20. The method of claim 15, wherein the at least one gas source includes a first gas source and a second gas source, and delivering a gas from at least one gas source includes:
delivering a first gas from the first gas source into the first section via the first port of the mask device; and
delivering a second gas from the second gas source into the second section via the second port of the mask device.

21. The method of claim 20, wherein the gas delivery system includes a first seal closing a first opening of the first gas source and a second seal closing a second opening of the second gas source, delivering the first gas includes removing the first seal to allow the first gas to flow into the first section, and delivering the second gas includes removing the second seal to allow the second gas to flow into the second section.

22. The method of claim 15, wherein the first photoactivating light and the second photoactivating light are delivered according to substantially different illumination parameters.

23. The method of claim 15, wherein:
the first photoactivating light is delivered to the first eye by a first illumination device;
the second photoactivating light is delivered to the second eye by a second illumination device; and
at least some of the delivery of the first photoactivating light occurs during at least some of the delivery of the second photoactivating light.

24. A system for treating eyes, comprising:
a mask device configured to be positioned over first and second eyes of a face, the mask device including an anterior side and a posterior side, the posterior side configured to be positioned proximate to the face and the anterior side configured to be positioned distally from the face, the mask device including an outer wall extending at least between the anterior side and the posterior side, the outer wall defining a chamber extending across the first and second eyes, the chamber including a first section and a second section, the first section configured to be positioned over the first eye, the second section configured to be positioned over the second eye, the anterior side including a first transmission region disposed over the first section and a second transmission region disposed over the second section, the first transmission region allowing a first photoactivating light for the first eye to be delivered into the first section, the second transmission region allowing a second photoactivating light for the second eye to be delivered into the second section;
at least one gas source storing a gas that is different than ambient air; and
a gas delivery system coupling the at least one gas source to the mask device, the gas delivery system configured to deliver the stored gas into the chamber of the mask device,
wherein the gas delivery system includes a first port leading into the first section of the chamber and a second port leading into the second section of the chamber, and
the at least one gas source includes a first gas source coupled to the mask device and including a first opening allowing a first gas to flow into the first section via the first port, and a second gas source coupled to the mask device and including a second opening allowing a second gas to flow into the second section via the second port.

25. The system of claim 24, wherein the gas delivery system includes a first seal closing the first opening of the first gas source and a second seal closing the second opening of the second gas source, the first seal configured to be removed to selectively allow the first gas to flow into the first section, the second seal configured to be removed to selectively allow the second gas to flow into the second section.

26. A method for treating eyes, comprising:
positioning a mask device over first and second eyes of a face, the mask device including an anterior side and a posterior side, the posterior side configured to be positioned proximate to the face and the anterior side configured to be positioned distally from the face, the mask device including an outer wall extending at least between the anterior side and the posterior side, the outer wall defining a chamber extending across the first and second eyes, the chamber including a first section and a second section, the first section configured to be positioned over the first eye, the second section configured to be positioned over the second eye, the anterior side including a first transmission region disposed over the first section and a second transmission region disposed over the second section;
at least one of delivering a first photoactivating light to the first eye via the first transmission region, or delivering a second photoactivating light to the second eye via the second transmission region; and
delivering a gas different than ambient air from at least one gas source into the chamber of the mask device, the at least one gas source being coupled to the mask device via a gas delivery system,
wherein the at least one gas source includes a first gas source and a second gas source, and delivering a gas from at least one gas source includes:
delivering a first gas from the first gas source into the first section via a first port of the mask device; and
delivering a second gas from the second gas source into the second section via a second port of the mask device.

27. The method of claim 26, wherein the gas delivery system includes a first seal closing a first opening of the first gas source and a second seal closing a second opening of the second gas source, delivering the first gas includes removing the first seal to allow the first gas to flow into the first section, and delivering the second gas includes removing the second seal to allow the second gas to flow into the second section.

* * * * *